United States Patent
Hess et al.

(10) Patent No.: US 9,841,046 B2
(45) Date of Patent: Dec. 12, 2017

(54) LOCKING FASTENER WITH DEFLECTABLE LOCK

(71) Applicant: Enduralock, LLC, Overland Park, KS (US)

(72) Inventors: Harold Hess, Leawood, KS (US); Tracy Hockenhull, Lenexa, KS (US); Warren Moore, Lenexa, KS (US)

(73) Assignee: ENDURALOCK, LLC, Overland Park, KS (US)

( * ) Notice: Subject to any disclaimer, the term of this patent is extended or adjusted under 35 U.S.C. 154(b) by 18 days.

(21) Appl. No.: 15/099,763

(22) Filed: Apr. 15, 2016

(65) Prior Publication Data

US 2016/0305465 A1    Oct. 20, 2016

Related U.S. Application Data

(60) Provisional application No. 62/193,437, filed on Jul. 16, 2015, provisional application No. 62/148,846, filed on Apr. 17, 2015.

(51) Int. Cl.
     *F16B 39/282*      (2006.01)
     *F16B 39/32*      (2006.01)
     (Continued)

(52) U.S. Cl.
     CPC ............ *F16B 39/282* (2013.01); *F16B 37/00* (2013.01); *F16B 39/24* (2013.01); *F16B 39/32* (2013.01); *F16B 39/34* (2013.01); *F16B 43/00* (2013.01)

(58) Field of Classification Search
     CPC ........ F16B 35/04; F16B 35/041; F16B 37/00; F16B 39/24; F16B 39/26; F16B 39/282; F16B 39/32; F16B 39/34; F16B 43/00
(Continued)

(56) References Cited

U.S. PATENT DOCUMENTS 687,774 A * 12/1901 Oliver .................... F16B 39/32
                                                          279/101
955,054 A      4/1910   Darby
(Continued)

FOREIGN PATENT DOCUMENTS

JP         07217634      8/1995
JP         H084743 A     1/1996
(Continued)

OTHER PUBLICATIONS

International Search Report and Written Opinion for PCT/US/2016/027744, 32 pages, dated Jul. 15, 2016.
(Continued)

*Primary Examiner* — Roberta S Delisle
(74) *Attorney, Agent, or Firm* — Armstrong Teasdale LLP

(57) ABSTRACT

A fastener with a locking mechanism includes an elongated bolt member with threaded segment defining a banking feature and generally planar surfaces, a nut member, a washer member, and a lock member. The nut member has a threaded bore for cooperating with the threaded segment of the bolt member and a peripheral edge with a flat side defining an axial slot. The washer member has a central bore with a banking portion that complements the banking feature of the bolt member such that, when the threaded segment is inserted in the central bore, the washer member moves axially and is rotatably fixed relative to the bolt member. The washer member has an axially projecting circumferential wall with radially inward facing engagement teeth for intermeshing with teeth of the lock member. The lock member has a spring finger upstanding from the annular body that is received in the axial of the nut member for fixing the lock member in rotation relative the nut member.

16 Claims, 8 Drawing Sheets

(51) Int. Cl.
*F16B 37/00* (2006.01)
*F16B 39/24* (2006.01)
*F16B 39/34* (2006.01)
*F16B 43/00* (2006.01)

(58) Field of Classification Search
USPC ......... 411/326, 327, 330–331, 431, 532–533
See application file for complete search history.

(56) References Cited

U.S. PATENT DOCUMENTS

| | | | |
|---|---|---|---|
| 961,371 A | 6/1910 | Posey | |
| 1,140,974 A | 5/1915 | Formby | |
| 1,142,345 A * | 6/1915 | Major | F16B 39/32 411/331 |
| 1,225,626 A | 5/1917 | Hannon | |
| 1,246,353 A | 11/1917 | Thigpen | |
| 1,249,336 A | 12/1917 | Cook | |
| 1,289,710 A | 12/1918 | Ervin | |
| 1,337,424 A | 4/1920 | Word | |
| 1,403,902 A | 1/1922 | Fields | |
| 1,526,914 A | 2/1925 | Kibler | |
| 2,018,574 A | 10/1935 | Richter | |
| 2,141,701 A | 12/1938 | Uherkovich | |
| 2,398,965 A | 4/1946 | Rounds | |
| 3,189,075 A * | 6/1965 | Jobe | F16B 35/041 411/272 |
| 5,190,423 A | 3/1993 | Ewing | |
| 5,460,468 A | 10/1995 | DiStacio | |
| 5,538,378 A | 7/1996 | Van Der Drift | |
| 5,575,602 A | 11/1996 | Savage et al. | |
| 5,597,278 A | 1/1997 | Peterkort | |
| 5,618,143 A | 4/1997 | Cronin, II et al. | |
| 5,713,708 A | 2/1998 | Van derDrift et al. | |
| 5,735,853 A | 4/1998 | Olerud | |
| 5,951,224 A | 9/1999 | DiStasio | |
| 6,010,289 A | 1/2000 | DiStasio et al. | |
| 6,082,941 A | 7/2000 | Dupont et al. | |
| 6,139,550 A | 10/2000 | Michelson | |
| 6,258,089 B1 | 7/2001 | Campbell et al. | |
| 6,261,291 B1 | 7/2001 | Talaber et al. | |
| 6,361,257 B1 | 3/2002 | Grant | |
| 6,383,186 B1 | 5/2002 | Michelson | |
| 6,398,783 B1 | 6/2002 | Michelson | |
| 6,413,259 B1 | 7/2002 | Lyons et al. | |
| 6,434,792 B1 | 8/2002 | Williamson | |
| 6,554,555 B2 * | 4/2003 | Imahigashi | H01Q 1/1214 411/149 |
| 6,602,255 B1 | 8/2003 | Campbell et al. | |
| 6,626,907 B2 | 9/2003 | Campbell et al. | |
| 6,695,846 B2 | 2/2004 | Richelsoph et al. | |
| 6,755,833 B1 | 6/2004 | Paul et al. | |
| 6,935,822 B2 | 8/2005 | Hartmann et al. | |
| 6,976,816 B2 * | 12/2005 | Slesinski | F16B 39/103 411/120 |
| 6,976,817 B1 | 12/2005 | Grainger | |
| 7,189,044 B2 | 3/2007 | Ball | |
| 7,270,509 B2 | 9/2007 | Disantis et al. | |
| 7,318,825 B2 | 1/2008 | Butler et al. | |
| 7,374,495 B2 | 5/2008 | Ball | |
| 7,621,943 B2 | 11/2009 | Michelson | |
| 7,763,056 B2 | 7/2010 | Dalton | |
| 7,857,839 B2 | 12/2010 | Duong et al. | |
| 7,887,547 B2 | 2/2011 | Campbell et al. | |
| 7,909,859 B2 | 3/2011 | Mosca et al. | |
| 7,955,037 B2 | 6/2011 | Disantis et al. | |
| 8,123,788 B2 | 2/2012 | Michelson | |
| 8,262,711 B2 | 9/2012 | Hess | |
| 8,366,365 B2 | 2/2013 | Disantis et al. | |
| 8,591,157 B1 * | 11/2013 | Stewart | F16B 31/02 411/10 |
| 2005/0207865 A1 | 9/2005 | Disantis et al. | |
| 2005/0209599 A1 | 9/2005 | Brunsvold | |
| 2006/0015104 A1 | 1/2006 | Dalton | |
| 2009/0060682 A1 | 3/2009 | Yeh et al. | |
| 2009/0192553 A1 | 7/2009 | Maguire et al. | |
| 2010/0121383 A1 | 5/2010 | Stanaford et al. | |
| 2011/0188970 A1 | 8/2011 | Dillon et al. | |
| 2012/0063864 A1 | 3/2012 | Hess | |
| 2014/0356097 A1 | 12/2014 | Hess et al. | |
| 2016/0084291 A1 * | 3/2016 | Stewart | F16B 39/32 411/327 |

FOREIGN PATENT DOCUMENTS

| | | |
|---|---|---|
| KR | 200241791 | 10/2001 |
| KR | 20100863200 | 10/2008 |
| KR | 2011-0099247 A | 9/2011 |

OTHER PUBLICATIONS

PCT International Search Report and Written Opinion dated Nov. 26, 2014 issued on corresponding PCT International Application No. PCT/US2014/051006.
International Preliminary Report (PCT/IB/373) and Written Opinion on Patentability (PCT/ISA/237) in corresponding International Application PCT/US2011/051189, dated Mar. 19, 2013.
TineLok: Overview, www.tinelok.com (2013).
TineLok, The Revolutionary Vibration-Proof Fastener System, www.tinelok.com (2013).
Written Opinion with International Search Report from Application No. PCT/US2011/051189, dated Jun. 28, 2012.

* cited by examiner

LOCKING FASTENER WITH DEFLECTABLE LOCK

CROSS-REFERENCE TO RELATED APPLICATIONS

This application claims priority to and the benefits of U.S. Provisional Patent Application No. 62/148,846 filed Apr. 17, 2015, and U.S. Provisional Patent Application No. 62/193,437 filed Jul. 16, 2015, each of which is incorporated by reference herein in its entirety.

BACKGROUND OF THE INVENTION

1. Field of the Invention

The subject invention is directed generally to fasteners, and more particularly to locking mechanisms for threaded fasteners.

2. Background of the Related Art

Fasteners commonly include mechanisms for ensuring that fastener elements do not loosen over time, potentially allowing joined elements to loosen or separate. Examples of mechanisms include thread bore inserts, and screw thread profiles that deform when tightened. Fasteners accessories like lock washers, cotter pins, and lock wires are also commonly used with fasteners to prevent fastener elements from loosening. Adhesive materials, like epoxy, can be applied to fastener threads to stake fastener elements to prevent fastener elements from loosening. Examples of mechanisms, fastener accessories, and adhesives are disclosed in U.S. Pat. No. 5,460,468 to DiStacio; U.S. Pat. No. 5,538,378 to Van der Drift; and U.S. Pat. No. 5,713,708 to Van der Drift et al., each of which is incorporated herein by reference. Conventional fastener mechanisms, accessories, and adhesive materials may not be suitable for some applications, such as high temperature environments or with structures subject to vibration.

Such conventional mechanisms, accessories, and adhesive materials have generally been considered satisfactory for their intended purpose. However, there is still a need in the art for improved fasteners. The present disclosure provides a solution for this need.

SUMMARY OF THE INVENTION

The subject invention is directed to a fastener locking mechanism including an elongated bolt member having a threaded segment with a banking feature, a washer member having a circumferential wall with radially inward facing engagement teeth and a banking portion that complements the banking feature of the bolt member, a lock member having an annular body with an upstanding spring finger and a tooth disposed on a radially outward surface of the annular body, and a nut member having a circumferential flat with an axial slot and a threaded bore corresponding to threaded segment of the bolt member. The banking feature of the bolt member cooperates with the banking portion of the washer member to fix the washer member in rotation relative to the bolt member. The spring finger of the lock member cooperates with the axial slot of the nut member to fix the lock member in rotation relative to the nut member. The tooth of the lock member is displaceable radially relative to the bolt member for engaging and disengaging the engagement teeth of the washer member. In a radially outer position, the tooth of the lock member intermeshes with the engagement teeth of the washer member to fix the lock member and nut member in rotation relative to the washer member. In a radially inner position, the tooth of the lock member is rotatable relative to the washer member such that the lock member and nut member are rotatable relative to the washer member and the bolt member.

In accordance with certain embodiments, the bolt member can include a flat. The flat can extend axially along a length of bolt member. The banking feature of the bolt member can include the flat. The flat can be radially adjacent to the threaded segment of the bolt member. The flat can be a first flat, and the bolt member can include one or more second flats. The banking feature can include both the first flat and the second flat. The second flat can extend axially along the bolt member. The second flat can be disposed on a side of the bolt member diametrically opposite the first flat. The threaded segment can extend circumferentially about the bolt member and couple the first flat with the second flat.

It is also contemplated that, in accordance with certain embodiments, the washer member can have opposed axial surfaces separated by an axial thickness of the washer member. A circumferential wall can extend from a periphery axially from a surface of washer member. Engagement teeth can be disposed an a radially inner surface of the circumferential wall. The engagement teeth can extend radially inward from the circumferential wall. A central aperture can extend through the thickness of the washer member between the axial surfaces of the washer member. The central aperture can include the banking portion that complements the banking feature of the bolt member. For example, one or more flat segments can bound the central aperture. The flat segment can correspond with the banking feature of the bolt member. The central aperture can include one or more arcuate segments bounding the central aperture. The arcuate segment can correspond to the threaded segment(s) of the bolt member. The central aperture can include both flat and arcuate segments, and a stress reduction feature can be disposed at an intersection of a flat segment and an arcuate segment.

In certain embodiments, the lock member can include a spring finger having a free end and a fixed end. The free end can be disposed radially inward of the fixed end. The fixed end can be connected to the annular body of the lock member. The tooth and the spring finger can be circumferentially aligned with one another. The annular body of the lock member can have a round, oval, square, rectangular, or any suitably shaped axial profile. The annular body can be deformable, for example becoming more round (or more elliptical) in response to inward force exerted on the spring finger at a location between the fixed and free ends of the spring finger. The spring finger can be a first spring finger, and the lock member can include a second spring finger connected to the annular body on a side of the annular body opposite the first spring finger.

In accordance with certain embodiments, the lock member can have a first and second teeth that each extend radially outward from the annular body of the lock member. The first and second teeth can be circumferentially adjacent to one another. The first and second teeth can also be circumferentially aligned to the spring tab. The first and second teeth can be disposed on opposite sides of the annular body of the lock member such that each extends radially in a direction opposite the other. The second tooth can be circumferentially aligned with a second spring finger of the lock member. It is also contemplated that more than one circumferentially adjacent tooth can be aligned to a first spring finger, and that more than one circumferentially adjacent tooth can be aligned to the second spring finger.

It is also contemplated that, in accordance with certain embodiments, the nut member can have an annular recess. The annular recess can have a diameter that is less than a diameter of the annular body of the lock member. The nut member can have a circumference with a plurality of faces. The plurality of faces of the nut member can form a hexagonal circumference extending about the nut member. One or more of the faces of the nut member can have an axial slot. The axial slot can extend between the annular recess and an end of the nut member opposite the annular recess of the nut member. It is contemplated that the nut member can have faces with axial slots disposed on faces that are diametrically opposed to one another.

In an aspect, the threaded segment and banking feature of the bolt member, central aperture and engagement teeth of the washer member, tooth and spring finger of the lock member, and axial slot of the nut member can cooperate as a locking mechanism. The locking mechanism can have a locked position wherein the annular body urges the lock member tooth radially outward such that the tooth intermeshes with the engagement teeth of the washer member, fixing the lock member in rotation relative to the washer member and preventing loosening of the nut member from the bolt member. The locking mechanism can have a tighten or release position wherein the annular body of the lock member urges the lock member tooth radially inward, rendering the lock member and nut member rotatable relative to the washer member and bolt member. It is contemplated that lock member can have a spring preload that normally urges the lock member tooth radially outward, and that a force exerted on the spring finger of the lock member can urge the lock member tooth radially inward to move to the reconfigure the locking mechanism from the locked position to the tighten or release position.

In another aspect, a spinal fixation system includes a fastener locking mechanism as described above and a rod. The rod seats in the bolt member and below the washer member. It is contemplated that tightening the nut member exerts force on the washer member which in turn urges the rod against the bolt member.

In certain embodiments, the bolt member can have a head portion coupled to an end of a stem section. The head portion can be fixed relative to the stem portion. A joint can be interposed between the head portion and the stem portion, the head portion thereby being movable relative to the stem portion. The head portion pivotable relative to the stem portion, such as in a conical movement envelope. The head portion can have a first threaded segment and the stem portion can have a second threaded segment. The first threaded segment can be a male threaded segment corresponding to a female threaded segment defined by the bore of the nut member. The second threaded segment can taper between an end adjacent to the head member and an end of the stem portion opposite the head portion. It is contemplated that the second threaded segment can have threads adapted for seating the bolt member to a bone structure, such as a pedicle.

In accordance with certain embodiments, the bolt member can include a tulip head. The tulip head can have a slot extending therethrough for seating the rod. The slot can be centrally disposed, extending across the top of the bolt member. The slot can be laterally disposed, extending across a side of the bolt member. Lobes can be defined on opposite sides of the slot. The lobes can have the banking feature of the bolt member defined thereon. The lobes can have the threaded segment of the bolt member defined thereon. In a contemplated exemplary embodiment, each lobe has portions of both the threaded segment and the banking feature defined thereon.

It is also contemplated that, in accordance with certain embodiments, the washer member can include a central bar portion. The central bar portion can extend across the washer member central aperture and divide the central aperture into first and second portions. One lobe of the bolt member tulip head can extend through the first portion of the central aperture, and the another lobe of the bolt member tulip head can extend through the second portion of the central aperture. The central bar portion can extend from the banking portion of the washer member such that, when the central bar portion is seated with the slot of the tulip head, the washer member is fixed in rotation relative to the tulip head. It is contemplated that central bar portion can seat slot of the tulip head, overlay the rod, and can be disposed between the nut member, lock member, and the stem of the bolt member.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those having ordinary skill in the art to which the disclosed technology appertains will more readily understand how to make and use the same, reference may be had to the following drawings.

DETAILED DESCRIPTION OF THE PREFERRED EMBODIMENTS

Figure 1:
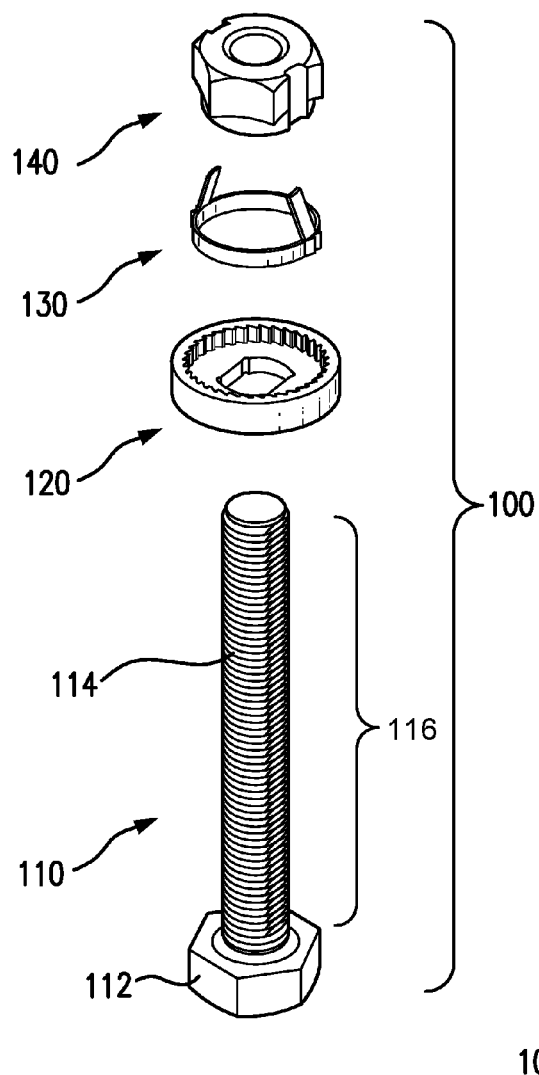
FIG. 1 is an exploded perspective view of a fastener device constructed in accordance with the present disclosure, showing a nut member, a lock member, a washer member, and a bolt member of the fastener device.

The present disclosure overcomes many of the prior art problems associated with threaded fasteners. In general, threaded fasteners are used to fixedly connect two or more pieces in a variety of applications such as, without limitation, with surgical implants, industrial applications, aerospace applications, and building applications. Among other features and benefits, the disclosed fastening devices and systems can provide one or more of quick and easy installation and/or removal, low torque requirements, vibration resistant secured tightness, and/or single end access for blind fastening applications. The advantages, and other features of the technology disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as upward, downward, left, right, up, down, length, height, width, thickness and the like are with reference to the Figures, and not meant in a limiting sense. Additionally, the illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed fastener assemblies. Additionally, the shapes and sizes of components are also exemplary and can be altered without materially affecting or limiting the disclosed technology.

FIG. 1 shows a fastener with a locking mechanism constructed in accordance with the present disclosure designated generally by reference numeral 100. Fastener device 100 generally includes an elongated bolt member 110, a washer member 120, a lock member 130, and a nut member 140. Bolt member 110 has a threaded segment 114. Threaded segment 114 includes male threads corresponding to female threads disposed on nut member 140. One or more of bolt member 110, washer member 120, lock member 130, and nut member 140 may include plastic, metal, a combination thereof, or any other suitable material.

Figure 2:
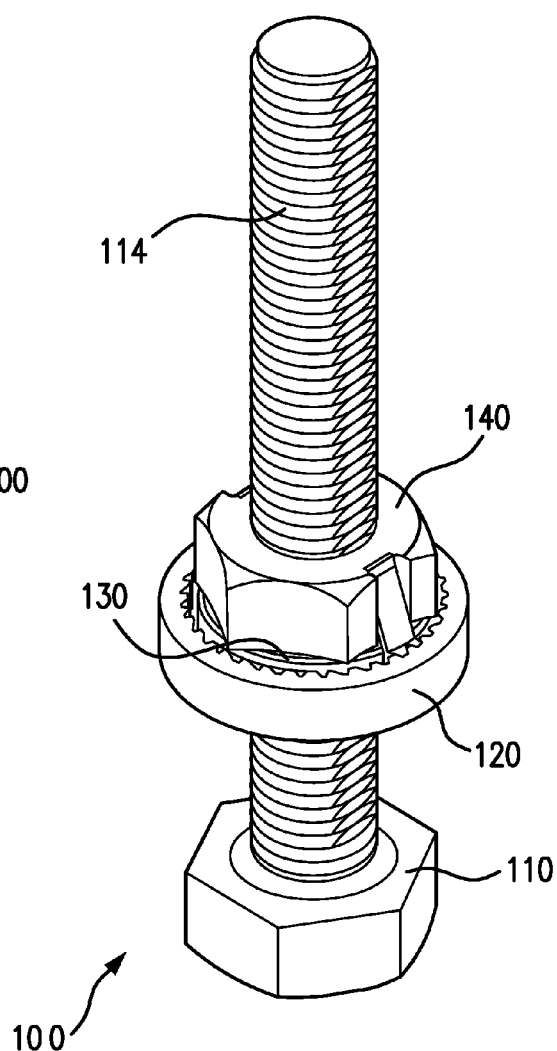
FIG. 2 is a perspective view of the fastener device of FIG. 1, showing the fastener device in an assembled configuration.

With reference to FIG. 2, washer member 120 seats about threaded segment 114 such that washer member 120 is rotatably fixed and axially displaceable relative to bolt member 110. Lock member 130 seats about threaded segment 114 of bolt member 110 and against an axial face of washer member 120. Nut member 140 has female threads that thread engage male threads on threaded segment 114, and is disposed axially along bolt member 110 such that nut member 140 seats against washer member 120. Lock member 130 seats about threaded segment 114 and is axially interposed between washer member 120 and nut member 140.

Figure 3:
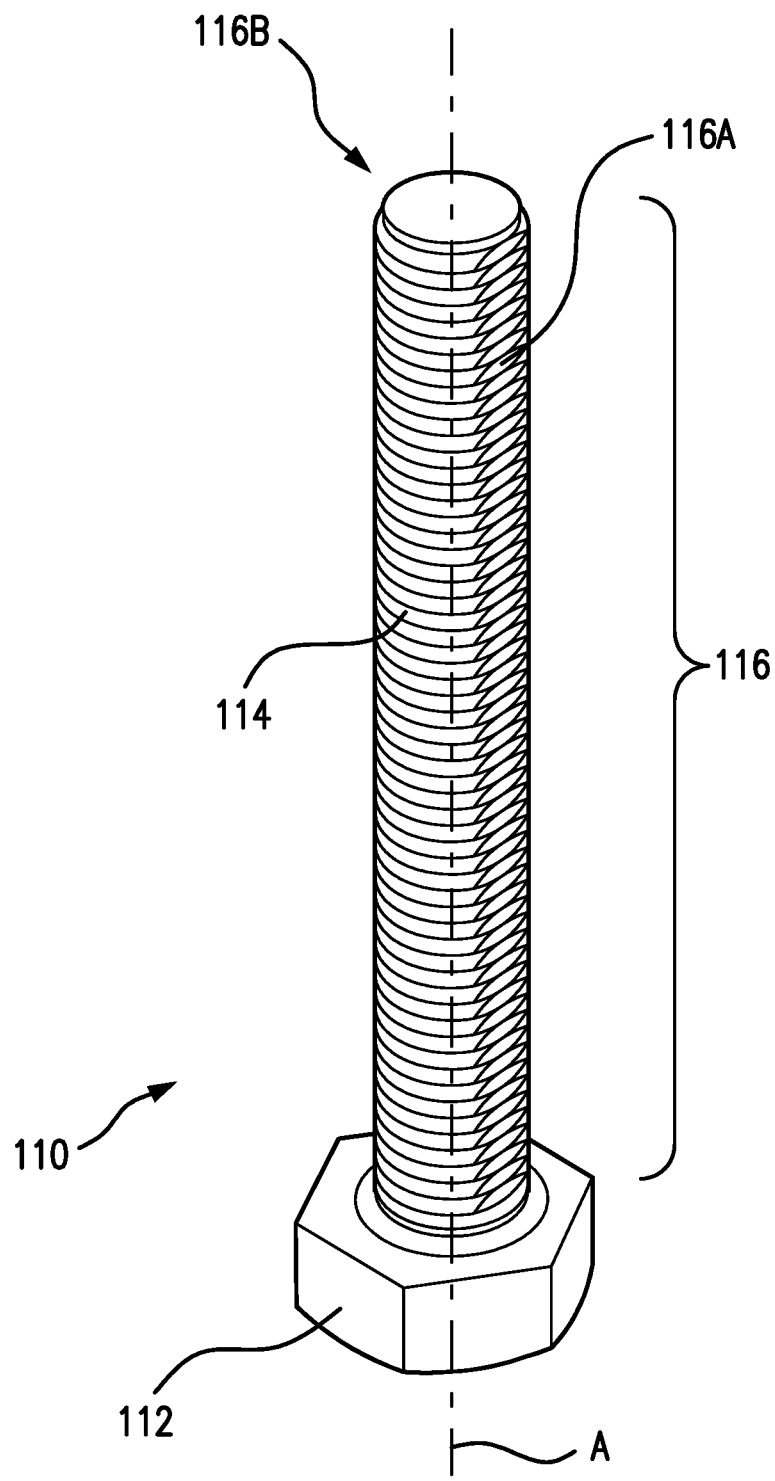
FIG. 3 is a perspective view of the bolt member of FIG. 1, showing the elongated body, threaded segment, and banking feature of the bolt member.

With reference to FIG. 3, an exemplary bolt member 110 is shown. Bolt member 110 defines a fastener axis A and, in the illustrated exemplary embodiment, includes a head portion 112 disposed on an end opposite threaded segment 114. Threaded segment 114 has a banking feature 116 that, in the illustrated exemplary embodiment, includes a first longitudinally extending flat 116A and an opposed second longitudinally extending flat 116B. It is to be understood and appreciated that other banking feature geometries are possible within the scope of the present disclosure such as a single flat portion, notches, grooves, convex portions, concave portions, protrusions, slots and/or combinations thereof. Examples of such features are shown and described in U.S. Patent Application Publication No. 2014/0308089 A1, the contents of which incorporated by reference herein in their entirely.

Figure 4:
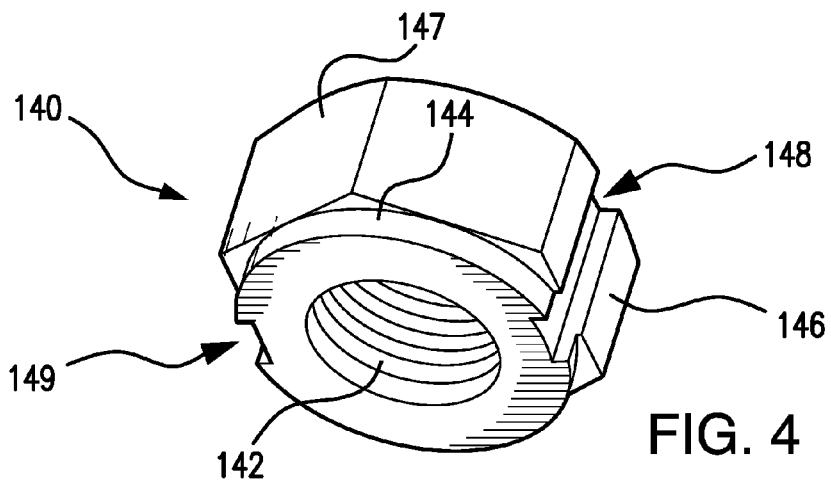
FIG. 4 is a perspective view of the nut member of FIG. 1, showing the threaded bore, annular recess, hexagonal recess, and an exemplary axial slot of the nut member.

With reference to FIG. 4, nut member 140 is shown. Nut member 140 includes a bore 142 having female threads, an annular recess 144, one or more slotted circumferential face 146, and one or more continuous face 147. Bore 142 extends between axially opposed faces of nut member 140. Annular recess 144 extends circumferentially about bore 142 and adjacent to the tool engagement faces of nut member 140. The one or more slotted circumferential face 146 and one or more continuous face 147 define tool engagement faces that extend axially between annular recess 144 and an axial face of nut member 140 that is opposite annular recess 144 and circumferentially about nut member 140. The tool engagement faces may correspond to one or more common tools, such as a wrench or socket, and in the illustrated exemplar embodiment define a hexagonal circumference. This allows for tightening or loosening nut member 140 using a common hand tool and without requiring use of a specialized tool.

The one or more slotted circumferential face 146 defines an axial slot 148. Axial slot 148 extends axially along slotted circumferential face 146 between annular recess 144 and the axial face of nut member 140 opposite annular recess 144, and has a circumferential width corresponding to the width of spring finger 134 (shown in FIG. 5) and spring finger 136 (shown in FIG. 5). This allows nut member 140 to cooperate with the preload of spring finger 134 such that, when axial slot 148 aligns in rotation about fastener axis A (shown in FIG. 3), spring finger 134 snaps into axial slot 148. As will be appreciated by those of skill in the art in view of the present disclosure, snapping spring finger 134 into axial slot 148 fixes lock member 130 in rotation relative to nut member 140.

In the illustrated exemplary embodiment shown in FIG. 4 axial slot 148 is a first axial slot and nut member 140 includes a second axial slot 149. Second axial slot 149 is disposed on a diametrically opposed side of nut member 140, i.e. on a side of axis A opposite first axial slot 148, and on a slotted face that is substantially parallel to slotted circumferential face 146. As will be appreciated by those of skill in the art in view of the present disclosure, nut member 140 can have one, two, or more than two axial slots. The number of axial slots on nut member 140 may correspond in number and circumferential position relative to those of lock member 130. Although two axial slots are shown in the illustrated exemplary embodiment, it is to be understood and appreciated that nut member 140 can have a single axial slot or more than two axial slots, as suitable for an intended application.

Figure 5:
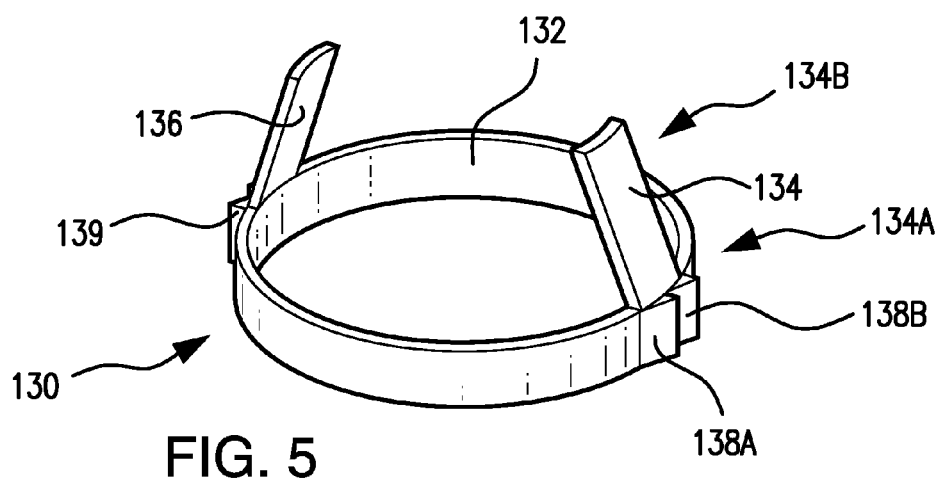
FIG. 5 is a perspective view of the lock member of FIG. 1, showing the deformable body, upstanding spring fingers, and teeth of the lock member.

With reference to FIG. 5, lock member 130 is shown. Lock member 130 includes a deformable annular body 132. In the illustrated exemplary embodiment annular body 132 has a ring-like shape. It is contemplated that annular body 132 may be round, oval, ellipsoid, or any other suitable shape, and is constructed from a resilient material, such as an elastomer or spring steel. Response to a radial force exerted thereon by one or more spring fingers 134, annular body 132 may become more or less round depending upon the amount of radial force exerted on annular body 132 and the spring constant of lock member 130.

Spring finger 134 upstands from annular body 132 and extends between a fixed end 134A and a free end 134B. Fixed end 134A connects to annular body 132. Spring finger 134 extends radially inward from fixed end 134A such that free end 134B is disposed radially inward of fixed end 134A. In the illustrated exemplary embodiment, spring finger 134 is a first spring finger and lock member 130 includes a second spring finger 136. Second spring finger 136 is similar to first spring tab 134, and is additionally connected to annular body 132 such that second spring finger 136 faces first spring finger 134 on a side of lock member 130 that is diametrically opposed to the first spring finger 134.

A tooth 138 is disposed on the radially outer surface of lock member 130 and is circumferentially aligned relative to spring finger 134. Tooth 138 includes a locking face 138B and a sliding face 138A that correspond to the locking faces and sliding faces of washer member 120 (shown in FIG. 4). This allows a tool, e.g. tool 10 (shown in FIG. 8), to slidably engage spring finger 134, thereby radially displacing tooth 138 relative to the engagement teeth 126 of washer member 120. In the illustrated exemplary embodiment, tooth 138 is one of a plurality of teeth, and a second tooth 139 is disposed on a diametrically opposite side of annular body 132 circumferentially adjacent to second spring finger 136. First tooth 138 and/or second tooth 139 can each be one of a plurality of circumferentially adjacent teeth arranged about the radially outer surface of annular body 132 for fixing lock member 130 in rotation relative to washer member 120 (shown in FIG. 6).

Figure 6:
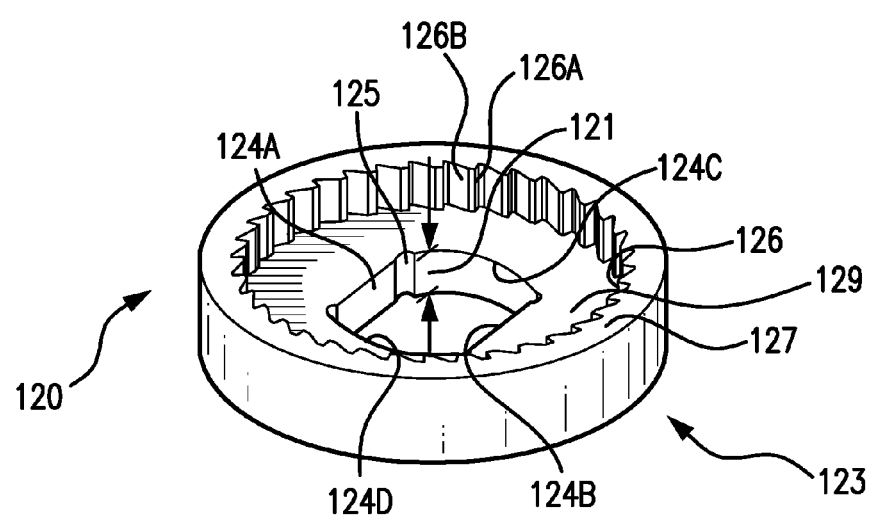
FIG. 6 is a perspective view of the washer member of FIG. 1, showing the washer member central aperture and banking portion, circumferential lip, and radial teeth oriented radially inwards relative to the circumferential lip.

With reference to FIG. 6, washer member 120 is shown. Washer member 120 has a central bore 121 that extends between a first axial face 129 and an opposed second axial face 123. First axial face 129 is separated from second axial face 123 by an axial thickness T of washer member 120. Central bore 121 is bounded by a plurality of banking segments that complement banking feature 116 of bolt member 110 (shown in FIG. 3). In the illustrated exemplary embodiment the plurality of banking segments includes pair of flats coupled by a pair of arcuate segments and a plurality of stress reduction features. In this respect central bore 121 includes a first flat 124A and a second flat 124B that bound central bore 121. A first arcuate segment 124C extends between first flat 124A and second flat 124B. A second arcuate segment 124D faces first arcuate segment 124C and extends between opposite ends first flat 124A and second flat 124B. Stress reduction features 125 are defined at corners of central bore 121 where respective flats and arcuate segments intersect one another. It will be appreciated that other banking segments are contemplated within the scope of the present disclosure.

A circumferential wall 127 extends axially from first axial face 129 about the periphery of washer member 120. Circumferential wall 127 has a plurality of engagement teeth 126. Engagement teeth 126 are distributed about a radially inner face of circumferential wall 127 and extend radially inward from circumferential wall 127 and towards central bore 121. In the illustrated exemplary embodiment, engagement teeth 126 include a locking face 126A that is substantially orthogonal with respect to circumferential wall 127 and a sliding face 126B that is oblique relative to circumferential wall 127.

Figure 7:
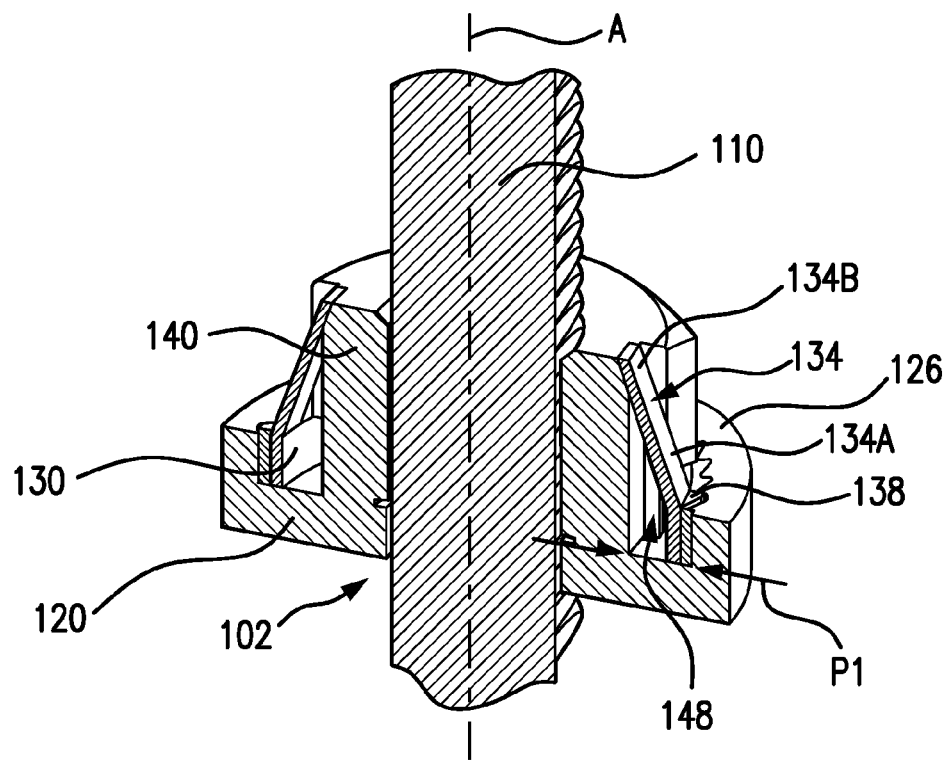
FIG. 7 is a perspective view of fastener of FIG. 1, showing the fastener and fastener locking mechanism in a locked position.
Figure 8:
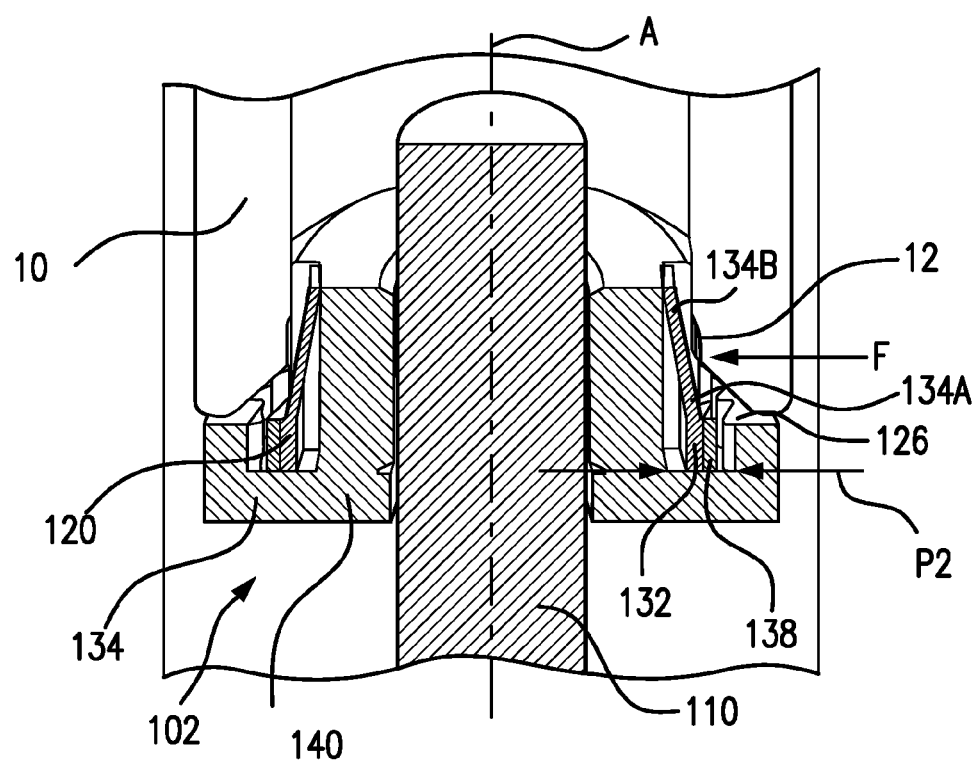
FIG. 8 is a perspective view of the fastener of FIG. 1, showing the fastener and fastener locking mechanism in a release or tighten position.

With reference to FIGS. 7 and 8, fastener 100 is shown in an assembled configuration. FIG. 7 shows fastener 100 with the locking mechanism 102 in a locked position. FIG. 8 shows fastener 100 with locking mechanism 102 in a tighten or release position. In the locked position shown in FIG. 7, washer member 120, lock member 130, and nut member 140 are each fixed both axially and in rotation relative to bolt member 110. In the tighten or release position shown in FIG. 8, lock member 130 and nut member 140 are both rotationally free relative to bolt member 110. As will be appreciated, rotation of nut member 140 relative to bolt member 110 displaces nut member 140 axially relative to bolt member 110, allowing corresponding axial displacement of washer member 120 and lock member 130 relative to bolt member 110.

As indicated in FIG. 7, fixed end 134A of spring finger 134 assumes a locked position radial offset P1 when locking mechanism 102 is in the locked position. At the locked position radial offset P1, deformable annular body 132 is urged radially outward at the circumferential position corresponding to spring finger 134. Urging annular body 132 radially outward at the location corresponding to spring finger 134 in turn urges tooth 138 of lock member 130 against engagement teeth 126 of washer member 120. Consequently, at circumferential arrangements where lock member tooth locking surface(s) 138A align and overlap in a coplanar arrangement with a corresponding locking surface 126A of engagement tooth 126, lock member 130 becomes rotational fixed relative to washer member 120.

As also indicated in FIG. 7, free end 134B of spring finger 134 seats within axial slot 148 when locking mechanism 102 is in the locked position. Seating free end 134B of spring finger 134 in axial slot 148 fixes lock member 130 in rotation with nut member 140. Fixing lock member 130 in rotation relative to nut member 140 causes lock member 130 to rotation with nut member 140. Consequently, when tooth 138 of lock member 130 seats against engagement teeth 126 of washer member 120, lock member 130 becomes fixed in rotation relative to washer member 120. As will be appreciated, since washer member 120 is fixed in rotation relative to both member the complementary banking member and banking portion of each, seating tooth 138 of lock member 130 against engagement tooth 126 also fixes nut member 140 in rotation relative to bolt member 110.

With reference to FIG. 8, fastener 100 is shown with locking mechanism 102 in the tighten or release position. Locking mechanism 102 moves from the locked position (shown in FIG. 7) to the illustrated tighten or release position by seating a tool over an end of fastener 100. In this respect tool 10 includes a finger contact surface 12 extending circumferentially about an interior recess of tool 10. Upon seating tool 10 seats over nut member 140 by axially displacing tool 10 relative to fastener 100, contact surface 12 comes into contact and exerts a contact force F on spring finger 134, oriented obliquely relative thereto, at a location between fixed end 134A and free end 134B of spring finger 134. Contact force F urges spring finger 134 radially inward relative to fastener axis A, deforming annular body 132 such that fixed end 134A of spring finger 134 assumes an unlocked or tighten radial offset P2.

Unlocked or tighten radial offset P2 is smaller than locked radial offset P1. Moving fixed end 134A of spring finger 134 from locked radial offset P1 to unlocked or release radial offset P2 causes the locking face 138B of tooth 138 to slide across locking face of engagement tooth 126. This disengages tooth 138 of lock member 130 from engagement tooth 126 of washer member 120, allowing lock member 130 and nut member 140 to rotate relative to washer member 120 and bolt member 110. As will be appreciated, tool 10 may be rotated either clockwise or counterclockwise about fastener axis A to displace nut member 140 axially in either direction along fastener axis A, tightening nut member 140 or loosening nut member 140 as appropriate. Thus, when a tool such as a conventional socket wrench is applied to nut member 140, lock member 130 is deflected radially inward such that teeth of lock member 130 disengage teeth of washer member 120, thereby allowing rotation of lock member 130 and nut member 140 relative to washer member 120 and bolt member 110.

Figure 9:
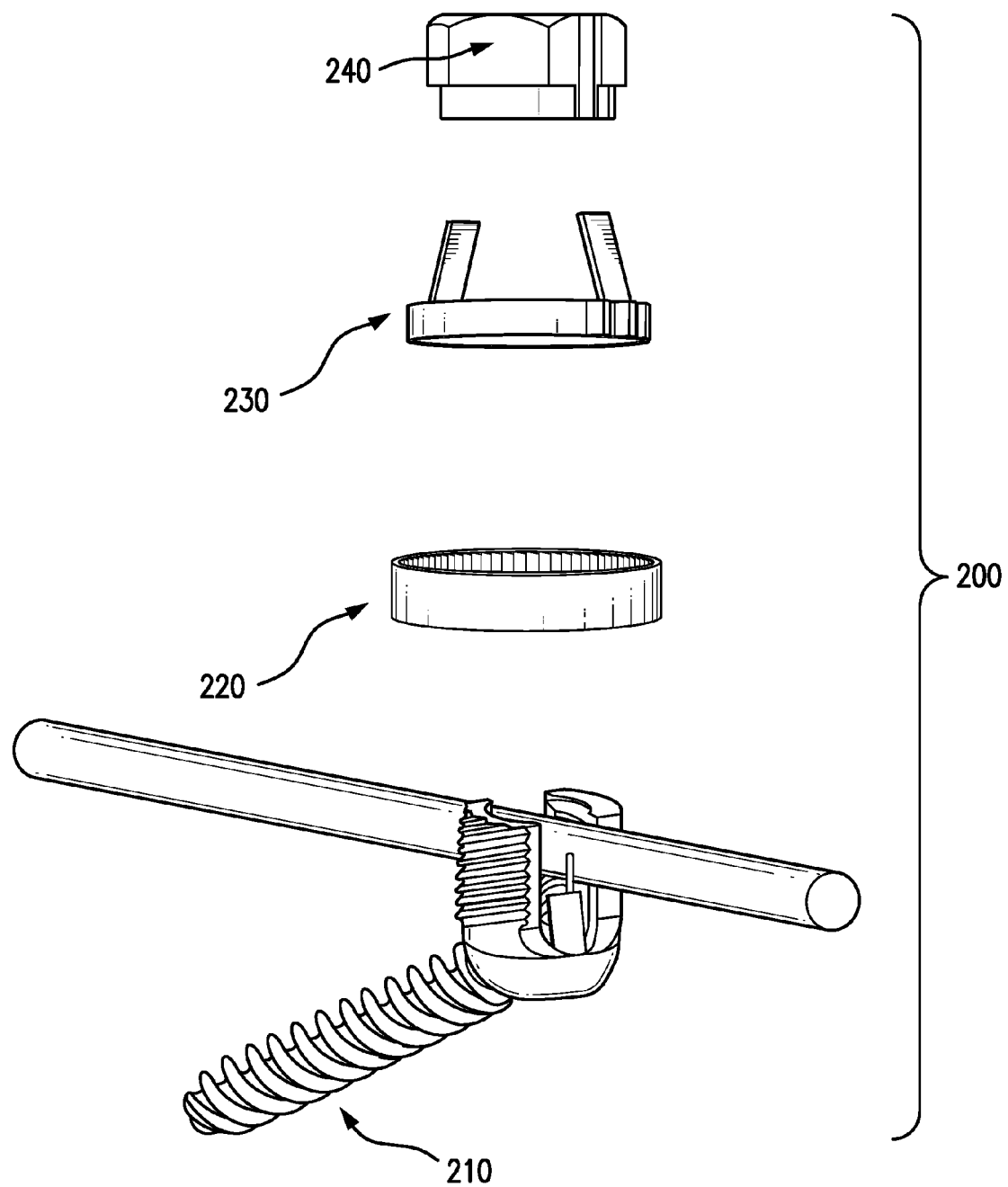
FIG. 9 is an exploded perspective view of another embodiment of fastener device constructed in accordance with the present disclosure, showing a bone fixation system including a locking mechanism in accordance with the present disclosure.

Referring now to FIG. 9, another embodiment of a fastener with a locking mechanism constructed in accordance with the present disclosure designated generally by reference numeral 200. Fastener 200 is similar to fastener 100 and generally includes an elongated bolt member 210, a washer member 220, a lock member 230, and a nut member 240. Nut member 240 is similar to nut member 140 (shown in FIG. 6). Lock member 230 is similar to lock member 130 (shown in FIG. 5).

Figure 10:
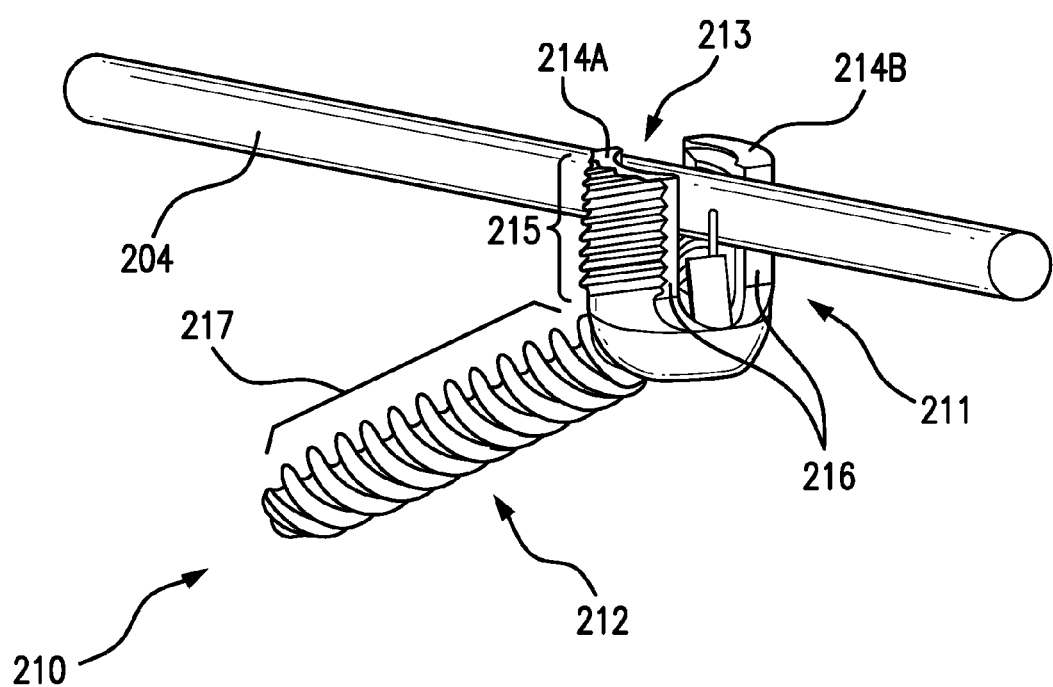
FIG. 10 is a perspective view of the bolt member of FIG. 9, showing the bolt member stem and tulip head.

With reference to FIG. 10, bolt member 210 is similar to bolt member 110, and is additionally configured as fixation system for coupling a rod 204 to bone, for example as a spinal pedicle screw rod system. Bolt member 210 includes a tulip head 211 and an elongated stem 212. Elongated stem 212 includes a second threaded segment 217 that tapers from an end adjacent to tulip head 211 to an end opposite tulip head 211, thereby facilitating insertion of elongated stem 212 into bone structure, such as a pedicle.

Figure 11:
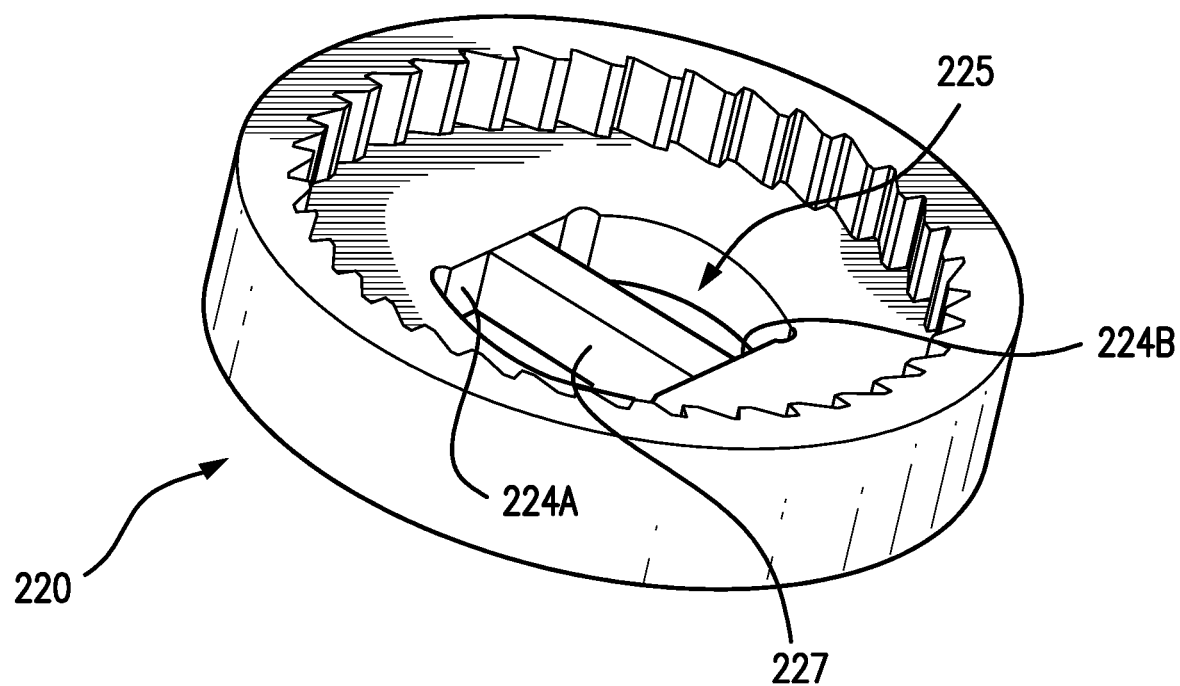
FIG. 11 is a perspective view of the washer member of FIG. 9, showing the washer member central bar portion.

Tulip head 211 includes a lateral slot 213 with a first prong 214A and an opposed second prong 214B. Tulip head 211 has a first threaded segment 215 with a banking feature 216. First threaded segment 215 has male threads that correspond to female threads defined within the central bore of nut member 240 (shown in FIG. 9). Banking feature 216 complements the banking feature of washer member 220 (shown in FIG. 11) such that washer member 220 is rotatably fixed and axially displaceable relative to tulip head 211. Banking feature 216 is split by lateral slot 213, thereby allowing for rod 204 to seat therein and to extend therethrough, allowing for rod 204 to be rotationally fixed and axially displaceable relative to tulip head 211. With reference now to FIG. 11, washer member 220 is shown. Washer member 220 is similar to washer member 120 and additionally includes a central bar portion 227. Central bar portion 227 is disposed within washer member central aperture 225 and extends between first flat 224A and second flat 224B of washer member banking portion 224. In this respect central bar portion 227 spans central aperture 225, allowing transfer of force from nut member 240 (shown in FIG. 9) in a force flow path including central bar portion 227 to rod 204 (shown in FIG. 10). As will be appreciated, central bar portion 227 extends between opposing sides of lateral slot 213 to create two discrete axial apertures on diametrically opposed flats of the tulip head banking feature.

Referring to FIGS. 9-11, the flats on first prong 214A (shown in FIG. 10) and second prong 214B are configured to mate with respective first flat inner surface 224A or second inner surface 224B of washer member 220. This rotationally fixes washer member 220 relative to tulip head 211 when first prong 214A and second prong 214B of tulip head 211 are inserted into the discrete axial apertures bounded by central bar portion 227. This allows axial movement of washer member 220 along the prongs of tulip head 211 to secure rod 204 within lateral slot 213 between washer member 220, lock member 230, and tulip head 211. After rod 204 is placed within lateral slot 213, washer member 220 is inserted over prongs of tulip head 211, and central bar portion 227 displaces axially downward within lateral slot 213 response to downward axial displacement of nut member 240 to rest against rod 204.

Those skilled in the art will readily appreciate that because nut member 240 and washer member 220 are substantially similar to nut member 140 and washer member 120, a common tool such as a wrench or socket can be used to tighten rod 204 to the fastener 100 or remove rod 204 from fastener 100 by either rotating nut member 240 clockwise or counterclockwise. Traditional bone fixation systems tend to require a significant amount of torque in order to lock a rod to a fastener or to remove the rod from the fastener. This can be the case, for example, in conventional external bone fixation systems and/or internal bone fixation systems like spinal pedicle screw rod systems. Those skilled in the art will readily appreciate, however, that embodiments of the present invention reduce the amount of torque required as compared with traditional spinal pedicle screw rod systems.

Figure 12:
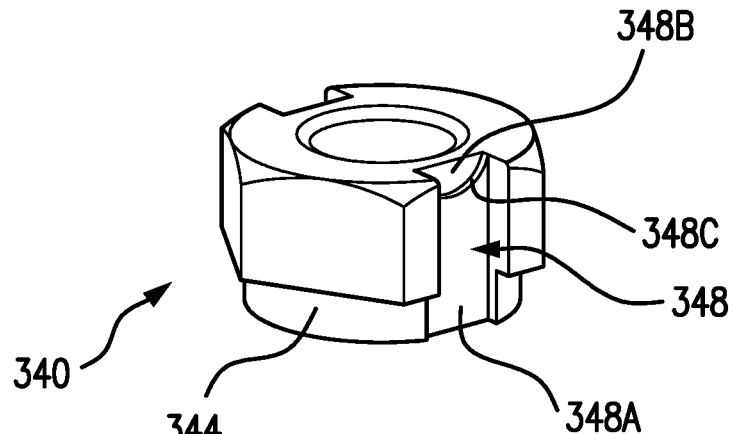
FIGS. 12-14 are perspective views of embodiments of nut member and lock member for the fasteners described herein, showing spring member protrusions and corresponding protrusion sockets define within the nut member axial slots.
Figure 13:
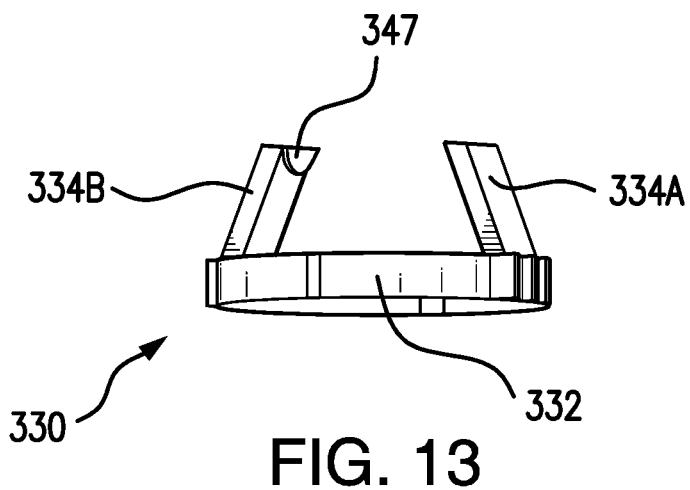
Figure 14:
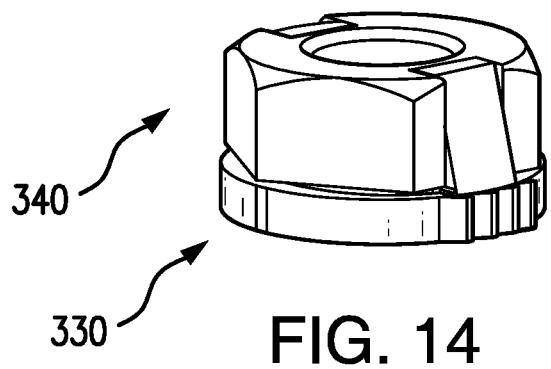

With reference to FIGS. 12-14, a nut member 340 and a lock member 330 are shown according to another embodiment. Referring to FIG. 12, nut member 340 is shown. Nut member 340 is similar to nut member 140 (shown in FIG. 6) and additionally includes a stepped axial slot 348. Stepped axial slot 348 has a first step 348A and a second step 348B. First step 348A traverses annular groove 344 and extends axially to second step 348B. Second step 348B is disposed radially inward of first step 348A. An arcuate riser 348C extends radially outward and faces axially.

Referring to FIG. 13, lock member 330 is shown. Lock member 330 is similar to lock member 130 (shown in FIG. 5) and additionally includes a stiffened deformable annular body 332, a stiffened first spring finger 334A, and a stiffened second spring finger 334B. As used herein, stiffened means that deforming annular body 332, first spring finger 334A, and/or second spring finger 334B requires more force than annular body 132, first spring finger 134, and/or second spring finger 136 (each shown in FIG. 5). This may be accomplished, for example, by thickening the respective elements relative to the counterpart elements shown in the embodiment illustrated in FIG. 5.

First spring finger 334A and second spring finger 334 both include a protrusion 347 (only one indicated in FIG. 13 for clarity reasons). Protrusion 347 corresponds second step 348B of stepped axial slot 348 (shown in FIG. 12), and in illustrated exemplary embodiment has an arcuate lip contoured to complement arcuate riser 348C (shown in FIG. 12) such that arcuate riser 348C seats in second step 348B (shown in FIG. 12). This allows for lock member 330 to seat against 340 and remain in an assembled configuration (shown in FIG. 14) prior to installation on a bolt member, simplifying fastening elements and error proofing the installation process.

Additional aspects and advantages of the present disclosure will become readily apparent to those skilled in this art from the following detailed description, wherein only exemplary embodiments of the present disclosure are shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

The fastening device technology described herein has unlimited application in industry and other uses. Particularly advantageous applications will involve use near motors or moving equipment in which vibration may cause loosening of traditional fasteners such as in automotive applications, aerospace applications, oil and gas, and manufacturing machinery. The present fastening device technology is also well suited for medical applications such as attaching pedicle screws to spinal rods, attaching spinal plates and fracture plates, fixing artificial joints, like hips and knees, orthopedic and maxillofacial external fixator systems, and the like. In particular, those skilled in the art will readily appreciate that embodiments of the fastening device technology described herein can withstand high temperature applications, for example, they can withstand temperatures as high as the material they are fabricated from can tolerate, and are easily applied, removed and reused. In addition, it is contemplated that the tightening of a nut number on a bolt member can be blind. For example, instead of the head portions, flats defined on the bolt member can be held or otherwise fixed during tightening.

While the subject invention has been described with respect to preferred and exemplary embodiments, those skilled in the art will readily appreciate that various changes and/or modifications can be made to the invention without departing from the spirit or scope of the invention as described herein and as defined by the appended claims.

What is claimed is:

1. A fastener with a locking mechanism, comprising:
   a) an elongated bolt member having a threaded segment with a banking feature with generally planar surfaces extending axially along the threaded segment;
   b) a nut member having a threaded bore extending therethrough for cooperating with the threaded segment of the bolt member, the nut member having a peripheral edge with at least one flat side with an axial slot therein;
   c) a washer member having a central bore formed therethrough with a banking portion that complements the banking feature of the bolt member so that, when the threaded segment of the bolt member is inserted in the central bore of the washer member, the washer member moves axially along the threaded segment and is fixed in rotation relative to the bolt member, the washer member further having an axially projecting circumferential wall with radially inward facing engagement teeth; and
   d) a lock member having an annular body and at least one upstanding spring finger that is angled radially inward from the annular body, the annular body of the lock member having at least one tooth disposed circumferentially adjacent to the at least one spring finger of the lock member and extending radially outward from the annular body of lock member.

2. A fastener as recited in claim 1, wherein the fastener has a locked position in which (a) the nut member engages the bolt member threaded segment such that the lock member spring finger engages the nut member axial slot, and (b) the lock member tooth intermeshes with the washer member engagement teeth such that the nut member is fixed in rotation relative to the bolt member.

3. A fastener as recited in claim 1, wherein the fastener has a tighten or release position in which (a) a tool engages the lock member spring finger such that the lock member tooth is displaced radially inward relative washer member engagement teeth, and (b) the lock member tooth disengages the washer member engagement teeth such that nut member is rotatable relative to the bolt member.

4. A fastener as recited in claim 1, wherein the lock member annular body is deformable for displacing the lock tooth radially between a radially outward, locked position, and a radially inward, tighten or release position.

5. A fastener as recited in claim 1, wherein the nut member has a hexagonal circumference with two diametrically opposing axial slots defined therein.

6. A fastener as recited in claim 1, wherein the nut member has an annular recess disposed on an axial end to accommodate an annular periphery of the washer body.

7. A fastener as recited in claim 1, wherein the nut member has a plurality of flat sides of which at least two have axial slots, wherein the lock member has a plurality of spring fingers that are received within diametrically opposed axial slots of the nut member.

8. A fastener as recited in claim 1, wherein the lock member has a shape selected from the group consisting of round, oval, ellipse, square, or rectangular, wherein the washer member and the nut member have complementary shapes.

9. A fastener as recited in claim 1, wherein the lock member has a plurality of teeth extending radially outward from the lock member annular body.

10. A fastener as recited in claim 1, wherein the lock member has first and second circumferentially adjacent teeth that are aligned with one of the plurality of lock member spring fingers.

11. A fastener as recited in claim 10, wherein the lock member has first and second diametrically opposed teeth that are aligned with first and second diametrically opposed spring fingers.

12. A fastener as recited in claim 1, wherein the washer member includes an annular periphery having engagement teeth extending radially inward therefrom.

13. A fastener as recited in claim 1, wherein the banking feature and banking portion are selected from the group consisting of: a flat portion; opposing flat portions; notches; grooves; convex portions; concave portions; protrusions; slots; and combinations thereof.

14. A fastener as recited in claim 1, wherein the bolt member, the nut member, the washer member, and the lock member are fabricated from plastic, metal, or combinations thereof.

15. A fastener as recited in claim 1, wherein the threaded segment has opposing flat sides and the washer member has opposing complementary flat portions.

16. A fastener as recited in claim 1, wherein the bolt member has a stem portion, wherein the threaded segment and banking feature are disposed on the stem portion of the bolt member.

* * * * *